(12) United States Patent
Zhang (10) Patent No.: US 12,138,480 B2
(45) Date of Patent: Nov. 12, 2024

(54) RADIATION THERAPY TREATMENT PLANNING

(71) Applicant: RaySearch Laboratories AB (Publ), Stockholm (SE)

(72) Inventor: Tianfang Zhang, Stockholm (SE)

(73) Assignee: Raysearch Laboratories AB (publ), Stockholm (SE)

( * ) Notice: Subject to any disclaimer, the term of this patent is extended or adjusted under 35 U.S.C. 154(b) by 197 days.

(21) Appl. No.: 17/906,201

(22) PCT Filed: Mar. 31, 2021

(86) PCT No.: PCT/EP2021/058505
§ 371 (c)(1),
(2) Date: Sep. 13, 2022

(87) PCT Pub. No.: WO2021/204633
PCT Pub. Date: Oct. 14, 2021

(65) Prior Publication Data
US 2023/0117544 A1   Apr. 20, 2023

(30) Foreign Application Priority Data
Apr. 6, 2020 (EP) ...................................... 20168169

(51) Int. Cl.
*A61N 5/10* (2006.01)
(52) U.S. Cl.
CPC .... *A61N 5/1031* (2013.01); *A61N 2005/1074* (2013.01)
(58) Field of Classification Search
CPC .................................................. A61N 5/1031
See application file for complete search history.

(56) References Cited

U.S. PATENT DOCUMENTS

2017/0361127 A1   12/2017   Ranganathan et al.
2018/0345042 A1*  12/2018   Voronenko ........... A61N 5/1081
(Continued)

FOREIGN PATENT DOCUMENTS

EP   3228356 A1   10/2017

OTHER PUBLICATIONS

Albin Fredriksson et al., "Maximizing the probability of satisfying the clinial goals in radiation therapy treatment plannin under setup uncertainty: Maximizing the probability of satisfying the clinical goals", Medical Physics vol. 42 No. 7, Jun. 10, 2015.
(Continued)

*Primary Examiner* — Chih-Cheng Kao
(74) *Attorney, Agent, or Firm* — Noréns Patentbyrå AB (57) ABSTRACT

A method and apparatus for generating a radiation treatment plan for a volume comprising:
receiving a first treatment plan upon which to base a second treatment plan, the first treatment plan indicative of a dose distribution; receiving at least one dose-distribution-derived function configured to provide a value based on at least part of the dose distribution; receiving a target for the respective value of each dose-distribution-derived function comprising receiving a probability distribution; determining an optimization problem, wherein the or each objective function is a function of the dose-distribution-derived function, the respective probability distribution and a respective loss function; performing the optimization process based on said optimization problem; and determining said second treatment plan.

14 Claims, 2 Drawing Sheets

(56) References Cited

U.S. PATENT DOCUMENTS

2019/0262077 A1    8/2019  Isola et al.
2020/0215352 A1*   7/2020  Fredriksson ......... A61N 5/1031

OTHER PUBLICATIONS

International Search Report & Written Opinion, European Patent Office, May 7, 2021, Rijswijk, Netherlands.
Tianfang Zhang, "Machine learning multicriteria optimization in radiation therapy treatmen planning", Sep. 6, 2019, Retrieved from the Internet URL: http://kth.diva-portal.org/smash/get/diva2:134858582/FULLTEXT.pdf.

* cited by examiner

RADIATION THERAPY TREATMENT PLANNING

TECHNICAL FIELD

This disclosure relates to an apparatus and method for radiation therapy treatment planning. In particular, the disclosure relates to an apparatus and method for radiation therapy treatment planning using an optimization process to derive a treatment plan. The disclosure also relates to an associated method and computer program.

BACKGROUND

Radiation therapy treatment planning may be performed for different types of radiation therapy, such as external beam radiation therapy based on photons, light ions, or electrons, or brachytherapy.

In the field of radiation therapy treatment, a key challenge is to devise a high-quality treatment plan. A treatment plan may define an amount of radiation to be applied to a target volume for therapy and, for example, an amount of radiation that may be received by one or more organs at risk (OARs) or other bodily tissue during said therapy. There are processes that enable the creation of treatment plans and, in particular, the improvement of treatment plans to ensure the desired radiation dose is received by a target volume, such as a tumour, while causing as little damage as possible to healthy tissue and preferably no damage at all to OARs, such as the heart or the spinal cord.

One approach to the creation or improvement of a treatment plan comprises an optimization process that uses mathematical optimization techniques. This optimization process is usually based on an optimization problem comprising a set of functions, wherein each function may represent an objective (i.e. an objective function) or a constraint (i.e. a constraint function). The functions used in the optimization problem may be, to at least some extent, incompatible in the sense that improvement in the output from one function may require a deterioration in the output from one or more of the other functions. The optimization process may be used to create a treatment plan in terms of starting with an idealized radiation dose distribution and optimizing to arrive at a set of parameters that define a deliverable treatment plan.

The objective functions and constraint functions used in the optimization problem may be considered quality measures for the treatment plan. An objective function may measure the deviation of a parameter from a desired value, typically related to the dose distribution.

The desired value of the parameter may be indicative of, for example, a minimum or maximum dose to a specific organ or volume. A constraint function may comprise a quality measure and/or define a set of feasible values the parameters may take. Thus, in one or more examples, the feasible values may be configured to take account of the technical limitations of the radiation therapy delivery device. The quality measures used as the functions should have mathematical properties that make them suitable for optimization, such as continuity and differentiability.

After an optimization problem has been defined, the most common way of arriving at a treatment plan is to find parameters representing said treatment plan in such a way that a weighted sum of the objective functions is minimized or maximized while the constraints are satisfied. When conflicting incentives exist among the constituent objectives in the total weighted sum objective, in order to ensure that the produced plan has properties aligned with the preferences of the planner, the weights are typically adjusted and re-optimizations performed in an iterative process until a plan of satisfactory quality has been found. As the functions used as objectives and constraints are usually not directly related to the criteria used for plan quality evaluation, this iterative process can be significantly time-consuming. There is thus a need for tools aimed more specifically at fine-tuning existing treatment plans—in particular, measuring more exactly the deviation between current and desired levels of plan quality metrics, and capturing more accurately the complexities in the preferences of the planner.

SUMMARY

According to a first aspect of the disclosure we provide a computer-implemented method for generating a radiation therapy treatment plan for a volume of a patient, the method comprising:

receiving a first treatment plan upon which to base a second treatment plan, the first treatment plan indicative of a dose distribution over said volume;

receiving at least one dose-distribution-derived function, the or each dose-distribution-derived function configured to provide a value as an output based on, as an input, at least part of the dose distribution in terms of at least part of the volume over which it is defined;

receiving a target for the respective value of each dose-distribution-derived function comprising receiving a probability distribution for each of, or groups of, the at least one dose-distribution-derived functions, the probability distribution representing the desirability of a range of the values output from said dose-distribution-derived functions for an input dose distribution;

determining an optimization problem comprising a total objective function, the total objective function comprising a sum of one or more objective functions, wherein the or each objective function comprises a function of one or more of the at least one dose-distribution-derived function, the respective probability distribution and a respective loss function;

performing the optimization process based on said optimization problem; and determining said second treatment plan from the optimization process.

In one or more examples, said step of receiving at least one dose-distribution-derived function comprises receiving at least two dose-distribution-derived functions.

In one or more examples, the probability distribution for each of, or groups of, the dose-distribution-derived functions represents a degree of preference or a degree of achievability for a range of the values output from said dose-distribution-derived functions for an input dose distribution around respective target values. In one or more examples, the most preferable target value may be located a peak or peaks of the probability distribution.

In one or more examples, the step of receiving the probability distribution comprises one or more of:

receiving user input that defines the probability distribution; and user selection of a probability distribution from a plurality of predetermined candidate probability distributions.

In one or more examples, the first treatment plan comprises one of:

a treatment plan defined in terms of operating parameters of a radiation therapy delivery device and from which a dose distribution over said volume can be derived;

a treatment plan defined in terms of the dose distribution; and a treatment plan defined in terms of irradiation intensity integrated over time from each direction in space and from which a dose distribution over said volume can be derived.

In one or more examples, the step of receiving dose-distribution-derived functions comprises one or more of:

receiving user input to define one or more of the dose-distribution-derived functions; and selection of one or more dose-distribution-derived functions from a set of candidate dose-distribution-derived functions, the candidate dose-distribution-derived functions determined based on the part of the body of the patient in which said volume is defined.

In one or more examples, said at least one dose-distribution-derived function comprise, for the whole volume or part thereof, one or more of dose-at-volume, volume-at-dose, average dose, homogeneity comprising a measure of the dose homogeneity in the whole or part volume, conformity index, and a penalty function, including minimum-dose, maximum-dose or a dose-volume histogram function.

In one or more examples, the at least one dose-distribution-derived functions comprise at least a first dose-distribution-derived function and a second dose-distribution-derived function, wherein:

the first dose-distribution-derived function comprises a function for use to improve the dose distribution for a selected sub-volume of said volume in the second treatment plan relative to the first treatment plan in response to said optimization process in that the first dose-distribution-derived function is configured, with its associated target, to provide a value indicative of an improvement for a desired change in the dose distribution for said selected sub-volume of said volume; and the second dose-distribution-derived function comprises a function for use to substantially maintain the dose distribution of one or more sub-volumes defined in the first treatment plan in the second treatment plan following said optimization process in that the second dose-distribution-derived function is configured, with its associated target, to provide a value indicative of a deterioration for any deviation in the dose distribution for one or more selected sub-volumes of said volume.

In one or more examples, the loss function is selected from one or more of:

a logarithmic loss function; and a cross-entropy loss function.

In one or more examples, the or each objective function comprises a function of one or more of the dose-distribution-derived functions, the respective target represented by a normal probability distribution centred on the target and a respective loss function. In other examples, a probability distribution having a form different to a normal distribution is used.

Thus, in one or more examples, the present method may be advantageous in that the dose-distribution-derived functions may be converted to objective functions for forming at least part of the optimization problem by the process of taking the dose-distribution-derived function and the probability distribution defining the target (which may, for example, comprise a normal distribution) and using it as input to the loss function. In one or more examples, the total objective function may comprise only objective functions converted from dose-distribution-derived functions by the present method.

In one or more examples, the method includes the step of: representing said probability distributions, for each dose-distribution-derived function, as a cumulative distribution function or a probability density function in the optimization problem.

In one or more examples, the step of performing the optimization process comprises: minimizing the total objective function and wherein the total objective function comprising a weighted sum of the one or more objective functions.

In one or more examples, the method comprises receiving an image of the volume and the dose distribution derived from the first and/or second treatment plan may be defined based on a plurality of voxels of said image. In one or more examples, the image comprises a plurality of voxels that define discrete sub-volumes of the image.

In one or more examples, the computer-implemented method is a method performed by a computing device. In one or more examples the method is performed by a computing device having an input device for receiving user input, a memory recall device for retrieving predetermined data from a memory and a processing device. In one or more examples, the steps of receiving a first treatment plan and/or receiving the at least one dose-distribution-derived function and/or receiving the target may be performed by the input device or the memory recall device. In one or more examples, the steps of determining an optimization problem and/or performing the optimization process and/or determining said second treatment plan may be performed by the processing device. In one or more examples, the computing device includes an output device which may output the determined second treatment plan to a further apparatus or to a user.

In one or more examples, the second treatment plan comprises data output from the apparatus which may be used to program a radiation therapy delivery device. In other examples, the second treatment plan may comprise data representing irradiation intensity integrated over time from each direction in space.

In one or more examples, the volume comprises a three-dimensional image and the dose distribution derived from the first and/or second treatment plan may be defined based on a plurality of voxels of said image, said voxels defining three-dimensional regions of the image.

According to a third aspect of the disclosure we provide an apparatus for generating a radiation therapy treatment plan, the apparatus comprising a processor and a memory and computer program code stored in said memory, the computer program code configured to, when executed by said processor, cause the apparatus to perform the method of the first aspect.

In one or more examples, the apparatus includes an input device configured to receive an input drawn by a user representing a probability distribution.

According to a further aspect we provide an apparatus for generating a radiation therapy treatment plan, the apparatus comprising means for or at least one processing module configured to:

receive a first treatment plan upon which to base a second treatment plan, the first treatment plan indicative of a dose distribution over a volume;

receive at least one dose-distribution-derived function, the or each dose-distribution-derived function configured to provide a value as an output based on, as an input, at least part of the dose distribution in terms of at least part of the volume over which it is defined;

receive a target for the respective value of each dose-distribution-derived function comprising receiving a probability distribution for each of, or groups of, the at least one dose-distribution-derived functions, the probability distribution representing the desirability of a range of the values output from said dose-distribution-derived functions for an input dose distribution;

determine an optimization problem comprising a total objective function, the total objective function comprising a sum of one or more objective functions, wherein the or each objective function comprises a function of one or more of the dose-distribution-derived functions, the respective probability distribution and a respective loss function;

perform the optimization process based on said optimization problem; and determine said second treatment plan from the optimization process.

In one or more examples, a plurality of means or processing modules may be provided to each perform one or more of the respective actions to receive a first treatment plan, receive at least one dose-distribution-derived function, receive a target, determine an optimization problem, perform the optimization process and determine said second treatment plan.

According to a further aspect we provide an apparatus or method for generating a plan that defines the delivery of radiation to a volume represented by an image comprising a plurality of voxels, said method defined by the steps of the first aspect using said image of the volume.

According to a third aspect of the disclosure we provide a computer program comprising instructions that, when executed by an apparatus having at least one processor, are configured to perform the method of the first aspect.

In one or more examples, the computer program is stored on a computer readable medium, such as a non-transitory computer readable medium.

BRIEF DESCRIPTION OF THE DRAWINGS

There now follows, by way of example only, a detailed description of embodiments of the invention with reference to the following figures, in which.

DETAILED DESCRIPTION

Radiation therapy treatment planning is a complex task with many different factors playing a part. The size and position of a tumour within the body, the position and sensitivity of organs, so called organs at risk, around the tumour, the technical capabilities of the radiation therapy delivery device, and the clinical outcome of historical radiation therapy treatment may all contribute to the determination of a treatment plan.

Figure 1:
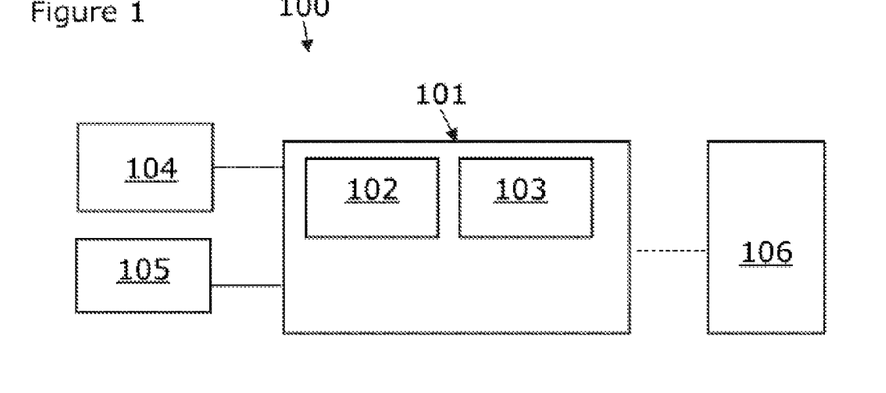
FIG. 1 shows an example apparatus for generating a radiation therapy treatment plan.

Example FIG. 1 shows an example treatment planning apparatus 100. The apparatus 100 may comprise a computer system 101 including a processor 102 and a memory 103 that is configured to perform a method defined by computer program code, which may be stored in said memory or otherwise provided to the computer system 101. It will be appreciated that the computer system 101 may comprise a terminal connected to a network, such as the Internet, and the processor and memory that perform the method may be located on one or more remote servers (not shown) with the terminal providing the interface to the user.

The treatment planning apparatus 100 may include an input device 104 to enable a user to enter information for performing treatment planning. In one or more examples, the input device 104 may enable preferences or other input to be entered on a graphical user interface. In one or more examples, the input device 104 may enable the user to draw an input pictorially. Accordingly, the input device 104 may comprise a stylus, mouse or touch screen interface among others. The treatment planning apparatus 100 may include a display device 105 coupled to the computer system 101 for display of information and/or presentation of the graphical user interface.

In one or more examples, the treatment planning apparatus 100 may be coupled to or be capable of being coupled to a radiation therapy delivery device 106 for delivery of radiation to a patient. Accordingly, the treatment plan determined using the treatment planning apparatus 100 may be provided to the radiation therapy delivery device 106 for subsequent delivery thereby. In one or more examples, the treatment plan may be translated into operating parameters of the radiation therapy delivery device 106 or the treatment plan may already be defined in terms of operating parameters of the radiation therapy delivery device 106.

It is common when performing treatment planning using optimization techniques to begin with a first treatment plan and make adjustments in an attempt to improve it. Such a process is known in the art as treatment plan optimization. However, it will be appreciated that the term "optimization" is used in the sense of gaining an improvement based on a defined measure rather than finding an absolute optimum solution. In general, an optimization of a treatment plan is a search for parameters of the treatment plan minimizing as best as possible some total objective function that evaluates the treatment plan subject to some constraints. For example, the parameters of the treatment plan may comprise operating parameters of the radiation therapy delivery device 106 (e.g. multi-leaf collimator positions, gantry rotation speeds over time, radiation beam power over time and any other operating parameter) and the total objective function may be defined in terms of calculated radiation dose distribution delivered to a volume based on those operating parameters and the constraints may comprise technical limitations of the device 106. In other examples, the parameters of the treatment plan may be a fluence map, wherein the parameters define the irradiation intensity integrated over time from each direction in space. Thus, it will be appreciated that the treatment plan may be defined in terms of many different types of parameters that define or are indicative of the radiation dose distribution over a volume of a patient to be treated. The dose distribution comprises a definition of how dose is distributed over a volume. The dose distribution may be defined in terms of the dose delivered to each of a plurality of voxels, the plurality of voxels comprising discrete volumes derived from an image of the volume be treated. In general, the treatment plan may define the delivery of radiation and the dose distribution in a volume may be derived therefrom.

In one or more examples, the starting point for the optimization process comprises a treatment plan having parameters corresponding to an already existing treatment plan, such as a previously delivered treatment plan for the current patient, which may have been determined by an optimization process itself (known in the art as a warm start). In one or more other examples, the starting point for the optimization may comprise a treatment plan having parameters in which a guess, such as a qualified guess based on the experience of a clinician, of their appropriate values has been made (known in the art as a cold start). For example, a cold start treatment plan may be defined in terms of one or more of randomly chosen plan parameters; or plan parameters which correspond to delivering an average dose in the target volume (or a target approximate to the target volume) equal to an associated prescribed dose level. The optimization process described herein is indifferent to whether the treatment plan is realizable, in that it represents a plan the device 106 is technically capable of delivering, or whether the treatment plan is idealized in that it may or may not be deliverable by the radiation therapy delivery device 106.

Thus, in summary, it will be appreciated that the first treatment plan may comprise a realistic treatment plan comprising one that is achievable given the constraints of the operating parameters of a radiation therapy delivery device, for example, or other constraints. In other examples, the first treatment plan may be an idealised treatment plan in that it may not have been determined whether it is achievable or not.

According to examples of the disclosure, it may be desired to make adjustments to the parameters of a treatment plan in an optimization process with respect to values obtained from dose-distribution—derived functions for a given dose distribution, wherein the dose distribution is derivable from the parameters of the treatment plan. By a dose-distribution— derived function, we mean any function taking a dose distribution (or part thereof) as an input and returning a number as output. Thus, the number output by the dose-distribution— derived function represents a dose-related measure, which can be used as a rating against a rating scale, wherein a further function may define the rating scale. The input to the dose-distribution—derived function may comprise the dose distribution over a plurality of voxels that represent the volume or part thereof to be treated.

Accordingly, the optimization process described in the examples herein may be configured to make adjustment to the parameters of a first treatment plan, determine a revised dose distribution for the volume based on the adjusted parameters and then assess the revised dose distribution, for example by using the outputs of the dose-distribution— derived functions. The solving or partial solving of the optimization may therefore lead to adjusted parameters which define a second treatment plan. The second treatment plan may be considered an improvement on the first treatment plan in view of the dose-distribution— derived function values achieved being closer to a respective dose-measure target. In practice, the second treatment plan may be such that its dose distribution differs relatively little from the original dose distribution of the first treatment plan in terms of some distance measure, which is either based on the three-dimensional dose distributions or on some collection of dose-distribution—derived functions. However, the optimization process may still yield a second treatment plan considered to be an improvement.

In other examples, the first treatment plan may be defined in terms of the dose distribution and the determination of the objective function or functions may include determining parameters of the second treatment plan and the optimization process may be configured to adjust the determined parameters of the second treatment plan and determine a revised dose distribution for the volume based on the adjusted parameters. The method may further include assessing the revised dose distribution, for example by using the outputs of the dose-distribution—derived functions.

Figure 2:
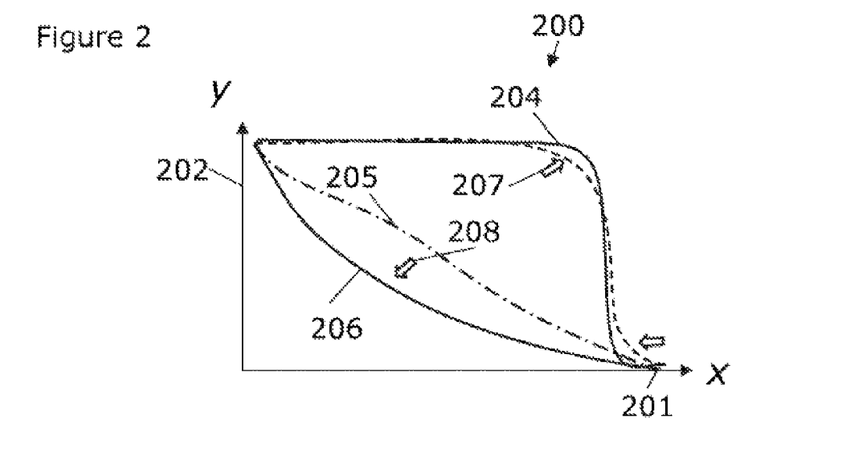
FIG. 2 shows an example dose-volume histogram from a first treatment plan and from a second treatment plan.
Figure 3:
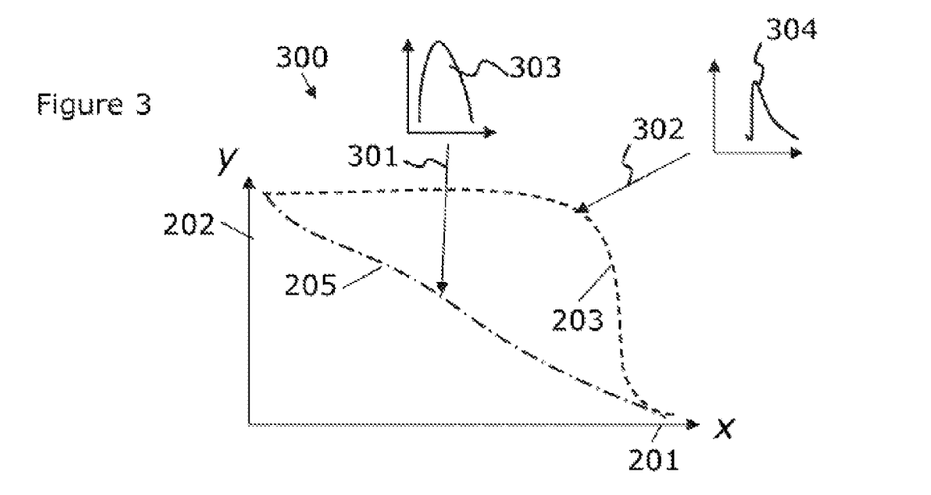
FIG. 3 shows the example dose-volume histogram from the first treatment plan and schematically shows the definition of a dose-distribution-derived function with an associated probability distribution.
Figure 4:
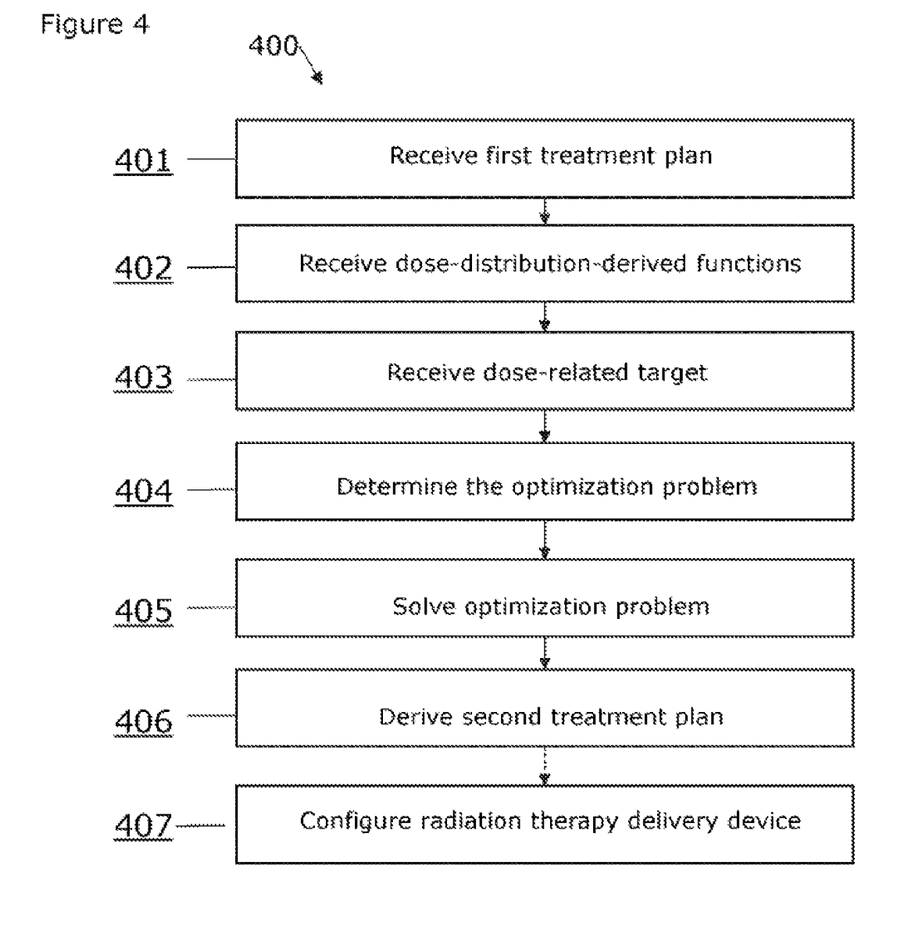
FIG. 4 shows a flow chart illustrating an example method for generating a radiation therapy treatment plan for a volume of a patient.

With reference to example FIGS. 2, 3 and 4 we will describe an example method 400 performed by said treatment planning apparatus 100.

The method relates to the generation of a radiation therapy treatment plan, termed the second treatment plan in the example that follows. The second treatment plan may comprise parameters that define how radiation should be delivered to a volume of a patient.

With reference to FIG. 4, step 401 comprises receiving a first treatment plan upon which to base a second treatment plan. Accordingly, in the example herein, the parameters of the first treatment plan are optimized to generate the second treatment plan.

The first treatment plan—and, likewise, the second treatment plan—is indicative of a dose distribution over said volume. Thus, a dose distribution over the volume can be calculated from the parameters of the first treatment plan (and/or the parameters of the second treatment plan). In one or more examples, the parameters of the first treatment plan are "complete" in that they uniquely determine the corresponding dose distribution. The first treatment plan may be defined in a variety of ways. In one or more examples, the first treatment plan has parameters that define the operating parameters of the radiation therapy delivery device 106 and a dose distribution over said volume is calculated therefrom. In one or more other examples, the first treatment plan has parameters that define the dose distribution. In one or more other examples, the first treatment plan has parameters that define irradiation intensity integrated over time from each direction in space, comprising a so-called fluence map, and the dose distribution over said volume is determined therefrom. The algorithms used to derive the resulting dose distribution from the parameters of the first treatment plan or parameters of the second treatment plan will be known to those skilled in the art.

The dose distribution may be determined based on a three-dimensional image of the volume of the patient that is discretized into a set of voxels, wherein each voxel or groups of voxels are assigned a value representing the dose that voxel or group of voxels would receive based on the first treatment plan (and subsequently, the second treatment plan, described below). The image typically comprises the output from a computed tomography (CT) scanner, such an x-ray or positron emission tomography-based scanner, or a magnetic resonance imaging (MRI) scanner, although other medical imaging techniques may be used.

Example FIG. 2 shows a dose-volume histogram 200. The x-axis 201 represents dose and the y-axis 202 represents the amount of a volume of interest. The lines 203 and 204 represents the dose in the tumour and therefore represents a first sub-volume of the volume of the patient. The lines 205 and 206 represents the dose in an organ at risk and therefore represents a second sub-volume of the volume of the patient. The dashed line 203 represents the dose delivered by the first treatment plan. The solid line 204 represents the dose that the clinician wishes to be delivered, after the present method, by the second treatment plan to the tumour (i.e. a more uniform dose). The dashed line 205 represents the dose delivered by the first treatment plan. The solid line 206 represents the dose that the clinician wishes to be delivered, after the present method, by the second treatment plan to the organ at risk (i.e. a lower dose).

Thus, it will be appreciated that in this example, the clinician may wish to change the uniformity of the dose to the tumour in the treatment plan as shown by arrow 207. It will also be appreciated that in this example, the clinician may wish to reduce the dose to the OAR in the treatment plan as shown by arrow 208. As will be described below, one or more dose-distribution-derived functions may be defined to achieve the changes 207 and 208.

Step 402 comprises receiving one or more dose-distribution-derived functions. Such functions may be known in the art as dose statistics or clinical goals. The clinician/user (or an AI) may specify or input the dose-distribution-derived functions to control the optimization process in a way that achieves effective treatment planning for the patient. The input may comprise one or more of regions of the volume, dose-related requirements or the functions themselves, as will be described below. Each dose-distribution-derived function comprises a function that provides a numeric value as an output based on, as an input, at least part of the dose distribution in terms of at least part of the volume over which it is defined. Accordingly, the dose-distribution-derived function may take as input the dose distribution over a sub-volume of the total voxels or the dose distribution over the whole volume. The numerical value will be termed the dose-measure value for ease of reference.

The dose-measure value output by the or each dose-distribution-derived function is to be used, in part, to drive the optimization. Thus, the dose-distribution-derived function is configured to output the dose-measure value which can be used to derive a rating. The rating may take a high value or a low value when the dose distribution provided to the associated dose-distribution-derived function is desirable relative to a target. The dose-distribution-derived functions may be determined by a user, such as a clinician, and/or may be selected from a set of candidate dose-distribution-derived functions.

Thus, in one or more examples, the step 402 of receiving the dose-distribution-derived functions comprises receiving user input, such as via input device 204, to define one or more of the dose-distribution-derived functions. The user input may comprise selecting a region in one or more images of the volume and associating with that selected region a dose-related requirement. The dose-distribution-derived function(s) may be determined based on this user input. Thus, in one or more examples, the user may define a sub-volume of the volume and enter a dose-related target, such as minimum dose, maximum dose or other target requirement, and the dose-distribution-derived function may be, at least in part, based on said user definition.

In one or more other examples, the step 402 comprises selection of one or more dose-distribution-derived functions from a set of candidate dose-distribution-derived functions. In one or more examples, the candidate dose-distribution-derived functions are determined based on the part of the body of the patient in which said volume is located.

Accordingly, predetermined dose-distribution-derived functions may be associated with different parts of the body and then selected as candidates based on the part of the body of interest. In one or more examples, the method may include the user identifying bodily organs in the volume or the computer system 201 identifying bodily organs in the volume, such as based on predetermined organ identification data, and presenting for selection a plurality of predetermined "candidate" dose-distribution-derived functions that are pre-associated with said identified organs.

The or each dose-distribution-derived function may be, for the whole volume or part thereof, a function that determines one or more of the dose-at-volume with respect to a predetermined part or all of the volume (such as in terms of a percentage of the volume), the volume-at-dose with respect to a predetermined dose level, or the average dose. The or each dose-distribution-derived function may be, for the whole volume or part thereof, a function that determines the homogeneity index with respect to a predetermined part or all of the volume (such as in terms of a percentage of the volume), representing the dose homogeneity in the target volume or sub-volume thereof. The or each dose-distribution-derived function may be, for the whole volume or part thereof, a function that determines the conformity index with respect to a predetermined isodose level. The conformity index of a treatment plan may be defined as a ratio between the volume covered by a reference isodose level and the target volume. It will be appreciated that there are a plurality of definitions of and algorithms for calculating homogeneity index and conformity index but for the purpose of this disclosure it does not matter which is used.

The or each dose-distribution-derived function may be, for the whole volume or part thereof, a penalty function, such as a quadratic-penalty function. Types of quadratic-penalty functions include minimum-dose functions, maximum-dose functions or dose-volume histogram functions.

A dose-distribution-derived function may be, for the whole volume or part thereof, a so-called single-voxel function with respect to some voxel, which outputs the dose delivered to said voxel. In one or more examples, the set of candidate dose-distribution-derived functions includes the corresponding single-voxel function for each of the voxels in the volume. Thus, in the above examples of the dose-distribution-derived functions, the reference to a part of the volume may comprise a single voxel in one or more examples.

In general, the dose-distribution-derived function may be any function taking as input the dose distribution and giving as output a single number for some region of interest of the volume (that is, a single voxel or a group of voxels). The number, i.e. the dose-measure value, comprises a dose-related statistic which may be compared to a dose-related target.

Step 403, described below, comprises receiving the dose-related target for the respective dose-measure value of each dose-distribution-derived function. Thus, the dose-measure value output by the dose-distribution-derived function may be assigned a target to move towards in the optimization process. Thus, a clinician may specify a target dose-measure that they wish to achieve by the optimization process.

In one or more examples, at least two dose-distribution-derived functions may be received. The at least two dose-distribution-derived functions may be of different "types", either to improve the dose distribution of part of the treatment plan or maintain the dose distribution of a part of the treatment plan. Thus, in one or more examples, the dose-distribution-derived functions comprise at least a first dose-distribution-derived function and a second dose-distribution-derived function.

The first dose-distribution-derived function may be a function for use to improve the dose distribution for a selected sub-volume of said volume in the second treatment plan relative to the dose distribution for the selected sub-volume in first treatment plan. It will be appreciated that said improvement is achieved by an optimization process, as will be described below. The first dose-distribution-derived function is therefore configured, with its associated target, in such a way that conformance of the dose-measure value (evaluated on the dose distribution derived from the second treatment plan) with respect to said associated target is indicative of an improvement for a desired change in said dose distribution for said selected sub-volume of said volume.

The second dose-distribution-derived function may be a function for use to substantially maintain the dose distribution of one or more sub-volumes defined in the first treatment plan in the second treatment plan. Thus, the second dose-distribution-derived function has the effect of maintaining the dose distribution for the sub-volumes during said optimization. The second dose-distribution-derived function is therefore configured, with its associated target, in such a way that unconformance of its dose-measure value (evaluated on the dose distribution of the second treatment plan) with respect to said associated target is indicative of a deterioration for any deviation in said dose distribution from the dose distribution of the first treatment plan for the selected sub-volume(s).

This combination of dose-distribution-derived function types may provide for effective control of the optimization that was not previously possible. Thus, while the variables of the optimization may comprise the parameters of the treatment plan, the dose-distribution-derived functions may comprise any criteria used for evaluation of the second treatment plan, which can, in one or more examples, provide for a more accurately targeted optimization than was previously possible and therefore a reduced need for possibly time-consuming, repeated optimizations in the process of reaching an improved second treatment plan. The use of dose-distribution-derived functions and their subsequent incorporation into the optimization process, as described below, more effectively aligns the desires of the clinician with the optimization problem that is solved.

As a practical example, the user (e.g. clinician) may want to satisfy certain clinical goals by making the dose-measure value of the dose-distribution-derived function evaluated on the dose distribution of the second treatment plan become smaller or larger than some associated threshold or target value. A corresponding dose-distribution-derived function is therefore defined for including in the optimization process.

The user may also want to preserve the quality of the second treatment plan, relative to the first treatment plan, in other aspects as best as possible. To achieve this, one or more second dose-distribution-derived functions may be generated in order to summarize the state of the current plan. The one or more second dose-distribution-derived functions may be designed to be such that a deterioration of their dose-measure values, relative to the target, based on the dose distribution of the second treatment plan implies a deterioration of the quality of the second treatment plan, relative to the first treatment plan.

In one or more examples, the one or more second dose-distribution-derived functions may be generated, for example, by determining dose-at-volume goals at (e.g. equally) spaced volume locations for one or more regions of interest selected by the user. In one or more examples, the one or more second dose-distribution-derived functions may be generated, for example, by determining, for each voxel of the regions of interest, the corresponding single-voxel function that maps the dose distribution to the dose in said voxel. A single-voxel function for the voxel with index i maps the dose distribution $d=(d\_1, \ldots, d\_n)$ to $d\_i$.

In one or more examples, the step 403 of receiving a target comprises receiving a probability distribution over the at least one dose-distribution-derived function. In one or more examples, the target or probability distribution may be specific to a particular one of the at least one dose-distribution-derived functions. However, in the example described herein the probability distributions for each dose-distribution-derived function are represented as a target for the set (e.g. a plurality) of dose-distribution-derived functions.

In such a case, the method may assume independence between the separate dose-distribution-derived functions and derive the probability distribution for the set. Alternatively, the method may use predetermined correlation data to derive the probability distribution for the set of dose-distribution-derived functions from the probability distributions for each of the constituent dose-distribution-derived functions, wherein the correlation data may be indicative of how different dose-distribution-derived functions may be inter-related to one another.

From the probability distribution a degree of preference or a degree of achievability for a range of dose-measure values of said dose-distribution-derived functions around some associated target values can be determined. It will be appreciated that degree of preference may represent the preference of a clinician and therefore the degree of preference may also be understood as a degree of acceptance of the dose-measure value relative to the target.

Thus, in one or more examples, the use of a probability distribution rather than single target values for the dose-distribution-derived functions may provide the ability to better represent the goals and preferences of the clinician user when performing treatment planning and/or may provide for more effective and efficient optimization because the degrees of clinical relevance/satisfactoriness associated with different dose-measure outputs from the dose-distribution-derived functions may be more effectively characterised by a probability distribution. Thus, in one or more examples, different nuances in clinical (un-)satisfactoriness associated with different outcomes of the second treatment plan is captured in the specification of said probability distribution. Thus, the use of a probability distribution instead of a single target value may be advantageous in that it can be seen as a "fuzzy" target value and may therefore provide more information for the optimization process than the use of a single target value. The use of a probability distribution compared to using a weight on the or each dose-distribution-derived function may also be advantageous because the probability distribution provides more information for the optimization process. More information for the optimization process may therefore lead to a more efficient and effective optimization process and therefore a more effective second treatment plan.

The step of receiving the probability distribution may comprise receiving user input, such as via input device 204, that defines the probability distribution. Thus, in one or more examples, the user input may represent a probability distribution drawn by a user and may therefore be indicative of a degree of preference for ranges of values of said one or more dose-distribution-derived functions. In other examples, the method may include generating a probability distribution based on one or more parameters inputted by the user that are indicative of one or more of the mean vector, the covariance and any other defining characteristics of said probability distribution that are specified for at least a range of dose-measure values.

In one or more examples, the step of receiving the probability distribution may comprise receiving a user selection of a probability distribution from a plurality of predetermined candidate probability distributions. The candidate probability distributions may have a variety of shapes, widths, mean vector or covariance and any other defining characteristics. The candidate probability distributions may be presented for selection by the user by the system 201. The candidate probability distributions displayed to the user for selection may undergo a filtering step based on a selected region of the volume, such as the selection of a particular bodily organ, to leave one or more candidate probability distributions most appropriate for the selected region based on predetermined filtering information.

In one or more examples, the predetermined candidate probability distributions may be based on historic data from other treatment plans and may therefore indicate the probability of achieving desired targets for a range of dose-measure values of the dose-distribution-derived functions based on what has been achieved historically.

In one or more examples, the probability distribution is represented as the composition of several probability distributions. Thus, for example, the probability distribution over the dose-measure values of a set of dose-distribution-derived functions may be represented by the associated probability distributions of each of said dose-distribution-derived functions. It will be appreciated that the associated probability distribution of the dose-measure value of each constituent dose-distribution-derived function can be determined from the joint probability distribution over all of said dose-distribution-derived functions.

The probability distribution may comprise a continuous function over a predetermined range of dose-measure values. For example, the predetermined range of dose-measure values may comprise a non-zero range that is specified by the user or may comprise a default setting of the method performed by the system 101.

Example FIG. 3 shows an annotated dose-volume histogram 300 representing the dose distributions 203, 205 of the first treatment plan shown in example FIG. 2, wherein two dose-distribution-derived functions are defined for the two different regions of the volume (the tumour and OAR), indicated by arrows 301 and 302. For each dose-distribution-derived function 301, 302 a probability distribution 303 and 304 is also defined.

In one or more examples, the probability distribution 303, 304 over the respective dose-distribution-derived function 301, 302, effectively assigns a corresponding likelihood of a dose-measure value (output from the dose-distribution-derived function given an input dose distribution) being achieved/acceptable/satisfactory in a treatment plan (i.e. the second treatment plan). The one probability distribution 303 is wide and symmetric, which may indicate that the clinician is accepting of a wider range of dose-measure values around the target dose-measure value. The other probability distribution 304 is narrower and skewed, which may indicate that the clinician is less accepting of dose-measure values on one side of a target dose-measure value than the other side.

The probability distribution 303, 304 over the respective dose-distribution-derived function 301, 302 is thereby designed in such a way that the tolerance in the dose-measure value of each dose-distribution-derived function for the second treatment plan is reflected. This provides flexibility in defining the preference of the user/clinician or what is achievable based on historic data. Thus, the clinician may enter a probability distribution having a peak centred on a desired dose-measure target with a small standard deviation if the associated dose-measure dose-distribution-derived function should be met strictly. Alternatively, a probability distribution having a peak centred on a desired target with a larger standard deviation may be used if the dose-measure target associated with the dose-distribution-derived function should be met less strictly. Different shaped probability distributions, which may be symmetrical or non-symmetrical may also be used, as required, to express the preferences of the clinician. Similarly, historical data may be indicative of how precisely dose-measure target may be met and the shape/defining characteristics of the probability distributions may reflect this.

For example, the tolerance in the dose-measure value of a dose-at-volume function in a treatment target is likely to be smaller than that for the dose-measure value of a dose-at-volume function in an organ at risk; also, they can be measured in different units, such as in cGy (e.g. for dose-at-volume) or dimensionless (e.g. for homogeneity index). The use of a probability distribution 303, 304 can account for these differences.

In more detail, once the set of dose-distribution-derived functions is defined, a probability distribution of a multidimensional real random variable, with dimensionality equal to the number, n, of dose-distribution-derived functions, may also be specified. Such a probability distribution may be derived from the probability distribution of each dose-distribution-derived function. A probability distribution of a n-dimensional random variable $X=(X_1, X_2, \ldots, X_n)$ is uniquely determined by its cumulative distribution function $F_X$ taking n real numbers as input and giving a number in the interval [0,1] as output, in such a way that $F_X(x_1, x_2, \ldots, x_n) \leq F_X(y_1, y_2, \ldots, y_n)$ for all pairs $(x_1, x_2, \ldots, x_n)$, $(y_1, y_2, \ldots, y_n)$ of realizations of x and Y, respectively, such that $x_i \leq y_i$ for all $i=1, 2, \ldots, n$;

$$\lim_{h \to 0^+} F_X(x_1, \ldots, x_{i-1}, x_i + h, x_{i+1}, \ldots, x_n) =$$
$$F_X(x_1, \ldots, x_{i-1}, x_i, x_{i+1}, \ldots, x_n) \text{ for all } i = 1, 2, \ldots, n;$$

$$\lim_{x_1, x_2, \ldots, x_n \to \infty} F_X(x_1, x_2, \ldots, x_n) = 1; \text{ and}$$

$$\lim_{x_i \to \infty} F_X(x_1, x_2, \ldots, x_n) = 0 \text{ for all } i = 1, 2, \ldots, n.$$

Thus, in one or more examples, the probability distribution for the set of dose-distribution-derived functions is represented as a cumulative distribution function. However, a probability distribution may be specified in different ways and the cumulative distribution function is only one way.

For each component $X_i$, the marginal cumulative distribution function $F_{X_i}$ is given by the integral:

$$F_{X_i}(x_i) = \int F_X(x_1, x_2, \ldots, x_n) dx_{j \neq i},$$

where $x_{j \neq i} = (x_1, \ldots, x_{i-1}, x_{i+1}, \ldots, x_n)$.

Thus, in one or more examples, the probability distribution is represented by the marginal cumulative distribution functions $F_{X_i}$, $i=1, 2, \ldots, n$. It will be appreciated that in one or more examples, it is sufficient to specify the marginal cumulative distribution function associated with each of the constituent dose-distribution-derived functions for the corresponding optimization problem to be fully defined. In one or more examples, one can recover the cumulative distribution function $F_X$ over X from the marginal cumulative distribution functions $F_{X_i}$ of all $X_i$ by additional assumptions on the distributional characteristics of X. Thus, in one or more examples, one assumes that X follows a multivariate normal distribution and that the correlation between each pair $X_i$, $X_j$ is given (e.g. by user input or as predetermined values); from this, the cumulative distribution function $F_X$ can be determined by a process which will be known to those skilled in the art.

As mentioned above, the first dose-distribution-derived function may comprise a function for use to improve the dose distribution for a selected sub-volume of said volume in the second treatment plan relative to the dose distribution for the selected sub-volume in first treatment plan. As a practical example, two first dose-distribution-derived functions with corresponding target values may be defined: "at least 5900 cGy at 95 percent volume of the target" and "at most 6100 cGy at 5 percent volume of the target", as examples.

Thus, we may assume that $x=(X_1,X_2)$ is a multivariate normal random variable with means 5900, 6100 and covariance matrix:

$$\begin{pmatrix} 50^2 & 0 \\ 0 & 50^2 \end{pmatrix}$$

Hence, the marginal cumulative distribution functions of $X_1, X_2$ are those of univariate normal distributions with means 5900, 6100 and standard deviation 50, respectively. The value 50 (cGy) is in this example used as a default parameter value but other standard deviation values may be used. The cumulative distribution function $F_X$ can thus be written as the product of the cumulative distribution functions of said univariate normal distributions.

As mentioned above one or more second dose-distribution-derived functions are designed to maintain the quality of the first treatment plan in the second treatment plan.

Accordingly, as an example, one may have a first treatment plan where the dose-at-volume values at volumes 10, 20, . . . , 90 percent are at 900, 800, . . . , 100 cGy, respectively, for some sub-volume of the volume, the sub-volume covering an organ at risk. In order to preserve the current state of the organ at risk dosage as best as possible, we may construct a multivariate normal distribution in the same fashion as described above so that the marginal distributions are univariate normal distributions with means 900, 800, . . . , 100 and standard deviations 200 (default parameter value). The value 200 (cGy) is in this example used as a default parameter value but other standard deviation values may be used.

In one or more other examples, the first treatment plan may only be defined in terms of a dose distribution or dose distributions of a set of historically delivered clinical plans (which is an example of the so-called cold start case). Accordingly, the method may be configured to evaluate the dose-distribution-derived functions on the historical dose distributions and generate an estimated Gaussian mixture model (in short, a combination of several normal distributions), from which marginal distributions are calculated. The mathematical process for calculating a marginal distribution from a Gaussian mixture model will be known to those skilled in the art.

Step 404 comprises determining the optimization problem to be solved. In general, step 404 may comprise determining a total objective function comprising the contributions from the or each dose-distribution-derived function and its corresponding target/probability distribution, and, if present, any constraints wherein a loss function is applied to each dose-distribution-derived function or an objective function derived therefrom. The total objective function may comprise weighted contributions from the objective functions.

Step 404 may include determining a set of objective functions upon which to perform the optimization process, i.e. solve or partially solve the optimization problem, each objective function of said set of objective functions being of at least one variable comprising a parameter that defines the second treatment plan, wherein the modification of the at least one variable is configured to affect at least one of the dose-measure values output by the dose-distribution-derived functions, and wherein the determination of the set of objective functions is based on the dose-distribution-derived functions and their respective targets (and optionally the probability distribution).

Accordingly, the first treatment plan may be defined in terms of a set of first parameters and the optimization process, described below, may provide for the determination of changes to the first set of parameters to yield a second set of parameters which define the second treatment plan. The objective functions may be defined in terms of one or more of those parameters. Alternatively, the first treatment plan may provide the dose distribution upon which the dose-distribution-derived functions are determined and the step 404 may include defining the objective functions that are of parameters that define the second treatment plan.

Step 404 may include converting the one or more dose-distribution-derived functions into objective functions, which may define the optimization problem, by applying a respective loss function to each dose-distribution-derived function and its associated probability distribution. In other examples, in which the step 403 comprises receiving a dose-measure target and not a probability distribution, step 404 may comprise converting the one or more dose-distribution-derived functions into objective functions, which may define the optimization problem, by applying a respective loss function to each dose-distribution-derived function and a default distribution, e.g. a normal distribution, centred on the dose-measure target.

An example of how to derive the one or more objective functions, and therefore the total objective function, from the dose-distribution-derived functions is as follows.

Steps 402 and 403 provide a set (e.g. one or more) of n dose-distribution-derived functions $\psi_1, \psi_2, \ldots, \psi_n$ of the dose distribution d and an associated probability distribution e.g. for the set.

To determine the total objective function $\Psi_{tot}$:

Let $\eta$ denote the plan parameters we use to represent the second treatment plan. The plan parameters may, for example, comprise operating parameters of the device 106 and from which a dose distribution can be derived, but in principle the plan parameters could be any parameters uniquely determining the dose distribution. It will be appreciated that the corresponding dose distribution $d=d(\eta)$ is completely determined by the plan parameters. The function $d_{(\eta)}$ that translates the plan parameters to a dose distribution may be predetermined or known to those skilled in the art.

The optimization problem defined in step 404 to be solved in step 405 is:

Minimize $\Psi_{tot}(\eta)$ subject to $\eta$ satisfying any constraints that may be user provided or technical constraints of the radiation therapy delivery device 106.

In one or more examples, the method may use the weighted-sum form $$\Psi_{tot}(\eta)=\Sigma_{i=1}^{M} w_i \Psi_i(\eta)$$

It will be appreciated that the M objective functions that form the total objective function may be equal to or less than the number n of dose-distribution-derived functions. Thus, in one or more examples, the two or more of a plurality of dose-distribution-derived functions may be combined into one objective function.

The setup may comprises the following steps:
1. Decide on the number of functions M and the weights $w_i$. The system 101 may receive user input to specify these values or may have default values. For example, M may equal two and the dose-distribution-derived functions may be split into two groups: single-voxel functions and non-single voxel functions. The functions of each of the two groups may therefore be combined into two objective functions.
2. For each i=1, 2, . . . , M:
   a. Decide on the index set $S_i$, which is a subset of all indices $\{1, 2, \ldots, n\}$. The system 101 may receive user input to specify $S_i$ values or a default value may be used.
   b. Decide on a parametrization of the probability distribution over the values of the dose-distribution-derived functions $\{\psi_j\}_{j \in S_i}$ in the index set, e.g. the cumulative distribution function $F_X$ or the probability density function $f_X$, where $x=(X_1, X_2, \ldots, X_n)$ is a vector-valued random variable. This can be decided by either user input or a predetermined algorithm. One example way is to use the probability density function for dose-distribution-defined functions of single-voxel type and a cumulative distribution function otherwise.
   c. Decide on a loss function L, taking as input the output of the parametrization in 2b and giving as output a number representing the loss contribution upon observing said output of the parametrization. For example, L could be the logarithmic loss L(t)=−log t or the cross-entropy loss L(t)=−a log t−(1−a) log(1−t), where a∈{0, 1}. Again, the choice of loss function may be received by user input or a predetermined loss function may be selected. In one or more examples, the choice of loss function may be based on the type of dose-distribution-defined function e.g. single voxel type or non-single voxel type.
   d. Depending on whether we used $F_X$ or $f_X$ (suppose the former), obtain $\Psi_i$ as $$\Psi_i(\eta) = L(F_X(\{\psi_j(d(\eta))\}_{j \in S_i}))$$

As an example, suppose that we want to group the dose-distribution-derived functions into lower/upper peak-seeking (get as low/high as possible), and tail-seeking (get as close to the mode as possible). We would then use the cumulative distribution function and the cross-entropy loss with a 0/1 for the former cases, and a probability density function and a log-loss on the latter case. Here, the index set represents the relevant indices of the functions.

Thus, to summarize, in one or more examples, the total objective function is sum of all objective functions, and each objective function is determined using one or more of the dose-distribution-derived functions and an associated probability distribution or target and a loss function. Thus, the total objective function $\Psi_{tot}$ inherently incorporates the dose-distribution-derived functions and the optional probability distribution. As described herein, the formulation of the optimization problem in this way is advantageous in terms of flexibility for selecting dose measures for guiding the optimization process.

As a more specific example, the method may be configured to determine a total objective function comprising at least one objective function based on a respective at least one dose-distribution-defined function by:
(i) receiving the set of dose-distribution-derived functions, partitioned into an index set $S_1$ of all constituent single-voxel functions and an index set $S_2$ of all constituent functions which are not single-voxel functions;
(ii) for each function in $S_1$ and $S_2$, receive the associated probability distribution represented as marginal cumulative distribution function;
(iii) assume independence between the dose-measure values of all functions in $S_1$ and $S_2$ and obtain two cumulative distribution functions, one for those in $S_1$ and one for those in $S_2$ (how to derive of a cumulative distributions from the marginal distributions and the independence assumption is known to those skilled in the art);
(iv) for $S_2$, apply a cross-entropy loss function on the corresponding cumulative distribution function, which will define one objective function $\Psi_2$;
(v) for $S_1$, differentiate to obtain from the cumulative distribution function from the corresponding probability density function and apply a log-loss function, which will define another objective $\Psi_1$;
(vi) use equal weights $w_1=w_2=1$ to obtain the total objective function as $\Psi_{tot}=\Psi_1+\Psi_2$.

In one or more examples, the present method is advantageous because it provides for greater flexibility in defining the optimization problem. In prior art methods, the objective functions are typically quadratic penalties. However, it may be desirable to perform the optimization process using one or more dose-distribution-derived functions (usually called clinical goals) which are not easily or cannot be directly optimized on in the prior art methods, so there has been a compromise wherein one optimizes on quadratic penalties in place of the dose-distribution-derived functions.

The present method may provide the added flexibility by, rather than using the dose-distribution-derived functions to assess each repetition of the optimization process, deriving objective functions directly from the dose-distribution-derived functions and their target and optional probability distribution. The method described herein of converting the dose-distribution-derived functions into objective functions that define the optimization problem using either the probability distribution or a dose-measure target in combination with a normal distribution, along with a loss function may provide for improved flexibility and effectiveness.

Step 405 comprises solving (or partially solving) the optimization problem determined in step 404. Thus, step 405 comprises finding variables (parameters of the second treatment plan) that minimize the total objective function subject to satisfying the constraints. The solving of the optimization problem defined in step 404 is conventional.

Step 406 may comprises determining said second treatment plan from the treatment plan parameters resulting from step 405.

Step 407 comprises an optional step of configuring or programming the radiation therapy delivery device 106 using the second treatment plan for delivery of radiation therapy in accordance with the second treatment plan.

The example method of the disclosure may be able to capture particular aims in terms of clinical goals when trying to fine-tune a treatment plan. The use of a novel total objective function reduces the need for finding particular weights of conventional penalty functions that correspond to the preferences of a clinician, which can be a time-consuming process. Also, since the formulation of the optimization problem may not contain nonlinear constraints, in one or more examples, one may be able to perform the optimization significantly faster.

The method described herein may be advantageous in one or more examples in that it provides the ability to choose arbitrary dose-distribution-defined functions to generate the total objective function. For example, one can directly put in evaluation criteria such as clinical goals. This allows for a natural way of fine-tuning an existing treatment plan by using said first and second dose-distribution-defined functions, as described above. Further, the probability distributions, in one or more examples, are able to capture nuances of the preferences of the user that are more complex than only using quadratic penalties. By receiving user input in the form of probability distributions instead, and by using appropriate loss functions, the total objective function is such that its value becomes very large when the plan is deemed unreasonable, which is more similar to the way a clinician may think when manually planning. In one or more examples, the method may also handle trade-offs between different goals more effectively due to the use of the probability distributions.

It will be appreciated that in one or more examples, the method includes the step of receiving one or more constraints, wherein the first treatment plan is defined in terms of a set of first parameters and the one or more constraints define values that the parameters of the second treatment plan can and/or cannot take in said optimization. For example, the first treatment plan may be defined in terms of parameters related to the radiation therapy delivery device 106 and the constraints may therefore relate to technical limitations of the radiation therapy delivery device, such as terms of maximum gantry rotation speeds or maximum power output. In other examples, the constraints may represent limits to the dose-distribution for the volume or sub-volumes thereof.

Figure 5:
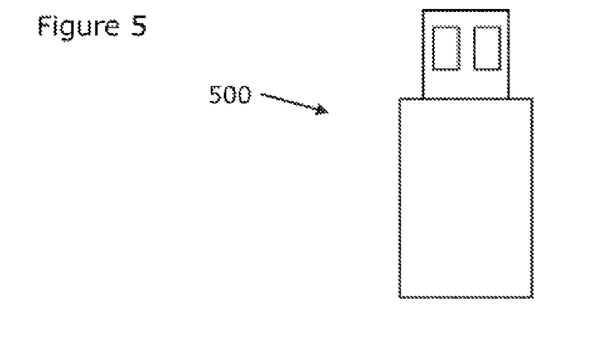
FIG. 5 shows an example computer readable medium.

Example FIG. 5 shows a computer readable medium 500, as an example of a computer program product. The computer readable medium may comprise a non-transitory computer readable medium. The computer readable medium 500 contains a computer program comprising computer program code that, when executed by an apparatus, such as computer system 201 having a processor 202 and memory 203, is configured to perform the method described herein.

The instructions and/or flowchart steps in the above figures can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

In some example embodiments the method steps described above are implemented as functional and software instructions embodied as a set of executable instructions which are effected on a computer or machine which is programmed with and controlled by said executable instructions. Such instructions are loaded for execution on a processor (such as one or more CPUs). The term processor includes microprocessors, microcontrollers, processor modules or subsystems (including one or more microprocessors or microcontrollers), or other control or computing devices. A processor can refer to a single component or to plural components.

In other examples, the methods illustrated herein and data and instructions associated therewith are stored in respective storage devices, which are implemented as one or more non-transient machine or computer-readable or computer-usable storage media or mediums. Such computer-readable or computer usable storage medium or media is (are) considered to be part of an article (or article of manufacture). An article or article of manufacture can refer to any manufactured single component or multiple components. The non-transient machine or computer usable media or mediums as defined herein excludes signals, but such media or mediums may be capable of receiving and processing information from signals and/or other transient mediums.

Example embodiments of the material discussed in this specification can be implemented in whole or in part through network, computer, or data based devices and/or services. These may include cloud, internet, intranet, mobile, desktop, processor, look-up table, microcontroller, consumer equipment, infrastructure, or other enabling devices and services. As may be used herein and in the claims, the following non-exclusive definitions are provided.

In one example, one or more instructions or steps discussed herein are automated. The terms automated or automatically (and like variations thereof) mean controlled operation of an apparatus, system, and/or process using computers and/or mechanical/electrical devices without the necessity of human intervention, observation, effort and/or decision unless otherwise indicated as requiring user input.

In this specification, example embodiments have been presented in terms of a selected set of details. However, a person of ordinary skill in the art would understand that many other example embodiments may be practiced which include a different selected set of these details. It is intended that the following claims cover all possible example embodiments.

The invention claimed is:

1. A computer-implemented method for generating a radiation therapy treatment plan for a volume of a patient, the method comprising:
   receiving a first treatment plan upon which to base a second treatment plan, the first treatment plan indicative of a dose distribution over said volume;
   receiving at least one dose-distribution-derived function, the or each dose-distribution-derived function configured to provide a value as an output based on, as an input, at least part of the dose distribution in terms of at least part of the volume over which it is defined;
   receiving a target for the respective value of each dose-distribution-derived function comprising receiving a probability distribution for each of, or groups of, the at least one dose-distribution-derived function, the probability distribution representing the desirability of a range of the values output from said at least one dose-distribution-derived function for an input dose distribution;
   determining an optimization problem comprising a total objective function, the total objective function comprising a sum of one or more objective functions, wherein the or each objective function comprises a function of one or more of the at least one dose-distribution-derived function, the respective probability distribution and a respective loss function;
   performing the optimization process based on said optimization problem; and
   determining said second treatment plan from the optimization process,
   wherein said second treatment plan is configured to deliver a radiation dose to the patient when the second treatment plan is executed on a treatment machine.

2. The computer-implemented method according to claim 1, wherein the probability distribution for each of, or groups of, the dose-distribution-derived functions represents a degree of preference or a degree of achievability for a range of the values output from said dose-distribution-derived functions for an input dose distribution around respective target values.

3. The computer-implemented method according to claim 1, wherein the step of receiving the probability distribution comprises one or more of:
receiving user input that defines the probability distribution; and
user selection of a probability distribution from a plurality of predetermined candidate probability distributions.

4. The computer-implemented method according claim 1, wherein the first treatment plan comprises one of:
a treatment plan defined in terms of operating parameters of a radiation therapy delivery device and from which a dose distribution over said volume can be derived;
a treatment plan defined in terms of the dose distribution; and
a treatment plan defined in terms of irradiation intensity integrated over time from each direction in space and from which a dose distribution over said volume can be derived.

5. The computer-implemented method according to claim 1, wherein the step of receiving dose-distribution-derived functions comprises one or more of:
receiving user input to define one or more of the dose-distribution-derived functions; and
selection of one or more dose-distribution-derived functions from a set of candidate dose-distribution-derived functions, the candidate dose-distribution-derived functions determined based on the part of the body of the patient in which said volume is defined.

6. The computer-implemented method according to claim 1, wherein said dose-distribution-derived functions comprise, for the whole volume or part thereof, one or more of dose-at-volume, volume-at-dose, average dose, homogeneity comprising a measure of the dose homogeneity in the whole or part volume, conformity index, and a penalty function, including minimum-dose, maximum-dose or a dose-volume histogram function.

7. The computer-implemented method according to claim 1, wherein the at least one dose-distribution-derived function comprises at least a first dose-distribution-derived function and a second dose-distribution-derived function, wherein:
the first dose-distribution-derived function comprises a function for use to improve the dose distribution for a selected sub-volume of said volume in the second treatment plan relative to the first treatment plan in response to said optimization process in that the first dose-distribution-derived function is configured, with its associated target, to provide a value indicative of an improvement for a desired change in the dose distribution for said selected sub-volume of said volume; and
the second dose-distribution-derived function comprises a function for use to substantially maintain the dose distribution of one or more sub-volumes defined in the first treatment plan in the second treatment plan following said optimization process in that the second dose-distribution-derived function is configured, with its associated target, to provide a value indicative of a deterioration for any deviation in the dose distribution for one or more selected sub-volumes of said volume.

8. The computer-implemented method according to claim 1, wherein the loss function is selected from one or more of:
a logarithmic loss function; and
a cross-entropy loss function.

9. The computer-implemented method according to claim 1, wherein the or each objective function comprises a function of one or more of the dose-distribution-derived functions, the respective target represented by a normal distribution centered on the target and a respective loss function.

10. The computer-implemented method according to claim 1, wherein the method includes the step of: representing said probability distributions, for each dose-distribution-derived function, as a cumulative distribution function or a probability density function in the optimization problem.

11. The computer-implemented method according to claim 1, wherein the step of performing the optimization process comprises:
minimizing the total objective function and wherein the total objective function comprising a weighted sum of the one or more objective functions.

12. An apparatus for generating a radiation therapy treatment plan, the apparatus comprising a processor and a memory and computer program code stored in said memory, the computer program code configured to, when executed by said processor, cause the apparatus to perform the method of claim 1.

13. The apparatus according to claim 12 wherein the apparatus includes an input device configured to receive an input drawn by a user representing a probability distribution.

14. A non-transitory computer program product for generating a radiation therapy treatment plan for a volume of a patient, the computer program product comprising a computer readable storage medium having program instructions embodied therewith that, when executed by a processor perform the method of claim 1.

* * * * *